US006235726B1

(12) United States Patent
Burns et al.

(10) Patent No.: US 6,235,726 B1
(45) Date of Patent: *May 22, 2001

(54) WATER INSOLUBLE DERIVATIVES OF POLYANIONIC POLYSACCHARIDES

(75) Inventors: James W. Burns, Framingham; Robert Miller, East Sandwich, both of MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/376,266

(22) Filed: Aug. 18, 1999

Related U.S. Application Data

(60) Division of application No. 08/914,320, filed on Aug. 18, 1997, now Pat. No. 6,030,958, which is a continuation-in-part of application No. 07/543,163, filed on Jun. 25, 1990, now Pat. No. 5,017,229, which is a continuation-in-part of application No. 07/100,104, filed on Sep. 18, 1987, now Pat. No. 4,937,270.

(51) Int. Cl.$^7$ .................................. A61K 31/735
(52) U.S. Cl. ............................. 514/57; 424/424; 514/54; 514/60; 514/944; 514/945; 514/964
(58) Field of Search .................... 514/54, 57, 60

(56) References Cited

U.S. PATENT DOCUMENTS

| | | | |
|---|---|---|---|
| 2,415,043 | * | 1/1947 | Rust ........................................ 536/30 |
| 2,937,164 | * | 5/1960 | Brown et al. ...................... 525/329.3 |
| 4,343,736 | * | 8/1982 | Uemura et al. ....................... 530/351 |
| 4,404,371 | * | 9/1983 | Bellmann et al. ...................... 536/98 |
| 4,526,714 | * | 7/1985 | Feijen et al. ......................... 530/363 |
| 4,798,724 | * | 1/1989 | Khanna ................................ 424/480 |
| 4,886,787 | * | 12/1989 | de Belder et al. ...................... 514/57 |
| 4,937,270 | * | 6/1990 | Hamilton et al. ..................... 514/777 |
| 4,973,493 | * | 11/1990 | Guire ....................................... 427/2 |
| 5,017,229 | * | 5/1991 | Burns et al. .......................... 106/162 |
| 5,676,964 | * | 10/1997 | Della Valle et al. ................ 424/423 |

FOREIGN PATENT DOCUMENTS 0 010 519 * 4/1980 (EP) .
0 416 250 * 3/1991 (EP) .

OTHER PUBLICATIONS

HCAPLUS record AN 1980:641468, Sachetto et al., EP 10519, Apr. 30, 1980.*

* cited by examiner

Primary Examiner—Gary Geist
(74) Attorney, Agent, or Firm—Genzyme Corporation

(57) ABSTRACT

A water insoluble, biocompatible composition that includes the reaction product of a polyanionic polysaccharide and an activating agent.

24 Claims, No Drawings

WATER INSOLUBLE DERIVATIVES OF POLYANIONIC POLYSACCHARIDES

BACKGROUND OF THE INVENTION

This application is a division of Ser. No. 08/914,320, filed Aug. 18, 1997, which is a continuation-in-part of U.S. Ser. No. 07/543,163 filed Jun. 25, 1990 now U.S. Pat. No. 5,017,229, which is a continuation-in-part of U.S. Ser. No. 07/100,104 entitled "Water-Insoluble Derivatives of Hyaluronic Acid" filed Sep. 18, 1987 now U.S. Pat. No. 4,937,270. The present invention relates to biocompatible films and gels formed from chemically modified polyanionic polysaccharides.

Hyaluronic acid ("HA") is a naturally occurring mucopolysaccharide found, for example, in synovial fluid, in vitreous humor, in blood vessel walls and umbilical cord, and in other connective tissues. The polysaccharide consists of alternating N-acetyl-D-glucosamine and D-glucuronic acid residues joined by alternating β 1–3 glucuronidic and β 1–4 glucosaminidic bonds, so that the repeating unit is -(1→4)-β-D-GlcA-(1→3)-β-D-GlcNAc-. In water, hyaluronic acid dissolves to form a highly viscous fluid. The molecular weight of hyaluronic acid isolated from natural sources generally falls within the range of $5 \times 10^4$ up to $1 \times 10^7$ daltons.

As used herein the term "HA" means hyaluronic acid and any of its hyaluronate salts, including, for example, sodium hyaluronate (the sodium salt), potassium hyaluronate, magnesium hyaluronate, and calcium hyaluronate.

HA, in chemically modified ("derivatized") form, is useful as a surgical aid, to prevent adhesions or accretions of body tissues during the post-operation period. The derivatized HA gel or film is injected or inserted into the locus between the tissues that are to be kept separate to inhibit their mutual adhesion. To be effective the gel must remain in place and prevent tissue contact for a long enough time so that when the gel finally disperses and the tissues do come into contact, they will no longer have a tendency to adhere.

Chemically modified HA can also be useful for controlled release drug delivery. Balazs et al., 1986, U.S. Pat. No. 4,582,865, states that "cross-linked gels of HA can slow down the release of a low molecular weight substance dispersed therein but not covalently attached to the gel macromolecular-matrix." R. V. Sparer et al., 1983, Chapter 6, pages 107–119, in T. J. Roseman et al., *Controlled Release Delivery Systems,* Marcel Dekker, Inc., New York, describes sustained release of chloramphenicol covalently attached to hyaluronic acid via ester linkage, either directly or in an ester complex including an alanine bridge as an intermediate linking group.

I. Danishefsky et al., 1971, Carbohydrate Res., Vol. 16, pages 199–205, describes modifying a mucopolysaccharide by converting the carboxyl groups of the mucopolysaccharide into substituted amides by reacting the mucopolysaccharide-with an amino acid ester in the presence of 1-ethyl-3-(3-dimethylaminopropyl)carbodiimide hydrochloride ("EDC") in aqueous solution. They reacted glycine methyl ester with a variety of polysaccharides, including HA. The resulting products are water soluble; that is, they rapidly disperse in water or in an aqueous environment such as is encountered between body tissues.

Proposals for rendering HA compositions less water soluble include cross-linking the HA. R. V. Sparer et al., 1983, Chapter 6, pages 107–119, in T. J. Roseman et al., *Controlled Release Delivery Systems,* Marcel Dekker, Inc., New York, describe modifying HA by attaching cysteine residues to the HA via amide bonds and then cross-linking the cysteine-modified HA by forming disulfide bonds between the attached cysteine residues. The cysteine-modified HA was itself water soluble and became water insoluble only upon cross-linking by oxidation to the disulfide form.

De Belder et al., PCT Publication No. WO 86/00912, describe a slowly-degradable gel, for preventing tissue adhesions following surgery, prepared by cross-linking a carboxyl-containing polysaccharide with a bi- or polyfunctional epoxide. Other reactive bi- or polyfunctional reagents that have been proposed for preparing cross-linked gels of HA having reduced water solubility include: 1,2,3,4-diepoxybutane in alkaline medium at 50° C. (T. C. Laurent et al., 1964, Acta Chem. Scand., vol. 18, page 274); divinyl sulfone in alkaline medium (E. A. Balasz et al., U.S. Pat. No. 4,582,865, (1986); and a variety of other reagents including formaldehyde, dimethylolurea, dimethylolethylene urea, ethylene oxide, a polyaziridine, and a polyisocyanate (E. A. Balasz et al., U.K. Patent Appl. No. 84 20 560 (1984). T. Malson et al., 1986, PCT Publication No. WO 86/00079, describe preparing cross-linked gels of HA for use as a vitreous humor substitute by reacting HA with a bi- or polyfunctional cross-linking reagent such as a di- or polyfunctional epoxide. T. Malson et al., 1986, EPO 0 193 510, describe preparing a shaped article by vacuum-drying or compressing a cross-linked HA gel.

SUMMARY OF THE INVENTION

The invention features a method for preparing a water insoluble composition by-combining a polyanionic polysaccharide and an activating agent under conditions sufficient to form the composition.

Preferred polyanionic polysaccharides include hyaluronic acid (HA), carboxymethylcellulose (CMC), carboxymethylamylose (CMA), chondroitin-6-sulfate, dermatan sulfate, heparin, and heparan sulfate; HA, CMC, and CMA are particularly preferred.

The preferred pH for carrying out the reaction is 3.5 to 8.0, more preferably 4.0 to 5.1 and most preferably 4.7 to 5.1. The preferred concentration for the polysaccharide is. 0.005–0.1M, more preferably 0.01–0.02M. The molar ratio of polysaccharide to activating agent is preferably 1 mole or less of carboxyl groups of polysaccharide per mole of carbodiimide, more preferably 1 mole of carboxyl groups of polysaccharide per 4 moles of carbodiimide. The preferred activating agent is a carbodiimide, e.g., 1-ethyl-3-(3-dimethylaminopropyl)carbodiimide and 1-ethyl-3-(3-dimethylaminopropyl)carbodiimide methiodide.

The activated-polyanionic polysaccharides which comprise the water insoluble compositions produced by the method of the invention may be in the form of a gel, or in the form of fibers. Blends can also be prepared by mixing various amounts of two or more different activated-polyanionic polysaccharides, more preferably blends consist of activated-HA and activated-CKC, or activated-HA and activated-CMA.

The compositions and blends of the invention may be provided in the form of an adhesion prevention composition, e.g., in the form of a film, foam, or composition suitable for incorporation in a syringe. They may also include a pharmaceutically active substance dispersed throughout making them useful as a drug delivery system. Suitable substances include proteins, growth factors, enzymes, drugs, biopolymers, and biologically compatible synthetic polymers.

The term "film", as used herein, means a substance formed by compressing a gel or fibers, or by allowing or causing a gel or fibers to dehydrate. Any gel or fibers of the invention may be formed into such a film.

The term "foam", as used herein, means a substance formed by introducing gas bubbles into the gels or fibers of the invention.

A "biocompatible" substance, as the term is used herein, is one that has no medically unacceptable toxic or injurious effects on biological function.

A "polyanionic polysaccharide" is a polysaccharide containing more than one negatively charged group, e.g., carboxyl groups at pH values above about pH 4.0.

We have discovered that a gel, foam, or film produced by treating a polyanionic polysaccharide with a suitable activating agent, may be made having decreased water solubility, without the use of any separately added bi- or polyfunctional cross-linking agent.

A "water soluble" gel, or film, as that term is used herein, is one which, formed by drying an aqueous solution of 1% weight/weight ("w/w") sodium hyaluronate in water, having dimensions 3 cm×3 cm×0.3 mm, when placed in a beaker of 50 ml of distilled water at 20° C. and allowed to stand without stirring, loses its structural integrity as a film after 3 minutes, and becomes totally dispersed within 20 minutes. A "water insoluble" film of the invention, as that phrase and like terms are used herein, formed using a 1% aqueous solution of a polyanionic polysaccharide, modified according to the invention, having the same dimensions and similarly allowed to stand without stirring in a beaker of 50 ml of distilled water at 20° C., is structurally intact after 20 minutes; the film boundaries and edges are still present after 24 hours, although the film is swollen.

A polyanionic polysaccharide is said to be "activated", as that term is used herein, when it is treated in an aqueous mixture in a manner that renders the carboxyl groups on the polyanionic polysaccharide vulnerable to nucleophilic attack; and an "activating agent" is a substance that, in an aqueous mixture including a polyanionic polysaccharide, causes the polyanionic polysaccharide to become so activated.

Because the gels and films are water insoluble, they can be thoroughly washed with water before use to remove unreacted substances.

Gels, foams, and films of the invention can also be prepared in colored form, by including a dye or stain in the reaction mixture. Such colored films and gels can be more easily seen when in place or during placement, making them easier to handle during surgical procedures than colorless ones.

The films, gels, and foams of the invention retain their strength even when hydrated. Because they adhere to biological tissues without the need for sutures, they are useful as postoperative adhesion prevention membranes. They can be applied to tissue even in the presence of bleeding.

Other features and advantages of the invention will be apparent from the following description of the preferred embodiments thereof, and from the claims.

DESCRIPTION OF THE PREFERRED EMBODIMENTS

Lysine-Modified HA

The gels, foams, and films of the invention are made generally as follows. HA is dissolved in water and the pH of the resulting aqueous mixture is adjusted downward; then the dissolved HA is activated by admixing a suitable activating agent, and a suitable lysine ester is admixed with the activated HA and allowed to stand until the desired gel has formed. The activating agent and the ester can be admixed in any sequence.

The preferred method of making the lysine-modified gels and films of the invention will now be described in more detail. As one skilled in the art will appreciate, gels and films of the invention can be made using protocols that are within the method of the invention yet are different in particulars from those described here.

A sample of hyaluronic acid or a salt of hyaluronic acid, such as sodium hyaluronate, is dissolved in water to make an aqueous mixture. HA from any of a variety of sources can be used. As is well-known, HA can be extracted from animal tissues or harvested as a product of bacterial fermentation. Hyaluronic acid can be produced in commercial quantities by bioprocess technology, as described for example in PCT Publication No. Wo 86104355. Preferably the concentration of HA in this first aqueous mixture is in the range between 0.4% and 2.5% weight/weight ("w/w"). Subsequent reactions are slower and less effective at significantly lower concentrations, while significantly higher concentrations are difficult to handle owing to their high viscosity.

The aqueous HA mixture should be acidic, preferably having a pH between pH 4.0 and pH 5.0, more preferably between pH 4.3 and pH 4.75. At lower pH values the preferred activating agent, EDC, is unstable, and at higher values the reaction rate is diminished. Preferably hydrochloric acid is added to adjust the pH, although other known acids can be used.

Once the pH of the aqueous HA mixture has been adjusted, an activating agent is admixed. Preferred activating agents include carbodiimides, most preferably EDC (in some references this substance is termed 1-(3-dimethylaminopropyl)-3-ethyl-carbodiimide or "DEC") or ETC (1-ethyl-3-(3-dimethylaminopropyl)carbodiimide methiodide).

Then a nucleophilic lysine ester is admixed to the aqueous HA-activating agent mixture. Preferred esters include methyl, ethyl, or t-butyl esters. The lysine can be in the form of di-lysine, tri-lysine, or polylysine, or their hydrochloride salts.

The lysine ester and the activating agent may be admixed to the pH adjusted HA mixture in any sequence, either all at once or gradually.

If a colored product is desired, a solution of a dye or stain such as the blue dye "Brilliant Blue R", also known as "Coomassie™ Brilliant Blue R-250", distributed as "Serva Blue" by Serva, can be admixed to the reaction mixture at this point. The resulting product has a blue color that can provide a good contrast to the color of body tissues, making the film or gel easy to see while it is handled during surgery and once it is in place.

Once the reagents (and the stain or dye, if any) have been admixed, the reaction mixture can be simply allowed to stand for a time, or it can be continually or occasionally stirred or agitated.

Upon admixing of the reagents the pH rises, and can be maintained at the desired pH by addition of acid as the reaction proceeds. We have found, however, that films and gels with various desired physical properties can be obtained by simply allowing the pH to rise as the reaction proceeds. The mode of addition of the reagents, particularly the EDC and the lysine ester, is not critical, but the ratios of these reagents to the HA is important. We have found that the best results are obtained when the ratio of HA:EDC:Lysine ester ranges from 1:2:1 to 1:4:10. Lower values typically result in weaker, less insoluble products, while higher values typically result in stronger, more insoluble products.

Polyanionic Polysaccharide-Modified HA

Polyanionic polysaccharide-modified HA gels and films are prepared generally by mixing HA (as described above) with a polyanionic polysaccharide and an activating agent to form a water-insoluble precipitate. The precipitate can be cast into thin membranes useful for postoperative adhesion prevention. It can also be colored to as described above. To increase the strength of films cast from the precipitate, the films may be subjected to dehydrothermal treatment in which they are heated under vacuum (about 30 mm Hg) at approximately 105° C. for 24 hr.

The polysaccharide and HA can be mixed together, after which the activating agent is added. Alternatively, the polysaccharide may be reacted with the activating agent, followed by addition of HA. A third option is to combine the HA with the activating agent, followed by addition of the polysaccharide. Preferred activating agents are as described above and include the carbodiimides EDC and ETC. The reaction is preferably carried out at a pH between 4 and 5. The preferred polysaccharide concentration ranges from 0.005 to 0.1M, and is more preferably in the range 0.01 to 0.02M. The preferred molar ratio of polysaccharide to activating agent is 1 mole or less of carboxyl groups of polysaccharide per mole of carbodiimide, more preferably 1 mole of carboxyl groups of polysaccharide per 4 moles of carbodiimide.

EDC-Activated Polyanionic Polysaccharides

Polyanionic polysaccharide gels, films, and foams are prepared generally by mixing at least one polyanionic polysaccharide (e.g., HA, CMC, CMA) with an activating agent to form a water-insoluble material. Preferred activating agents are as described above and include the carbodiimides EDC and ETC. The reaction may be carried out at a pH between 3.5 and 8, with optimal reaction conditions occurring between pH 4.7 and 5.1. The preferred polysaccharide molecular weight used in the reaction may range from $9.0 \times 10^4$ to $3.0 \times 10^6$ daltons, but preferably is between $2.5 \times 10^5$ to $1.0 \times 10^6$ daltons. The preferred molar ratio of carboxyl groups of polysaccharide to activating agent is 1 mole or less of carboxyl group of polysaccharide per mole of carbodiimide, more preferably 1 mole of carboxyl groups of polysaccharide per 4 moles of carbodiimide. The insoluble material formed by this method may be in the form of a gel or in the form of fibers and can be used directly for adhesion prevention or drug delivery, or can be cast onto flat molds and either air dried or lyophilized to yield thin films or foams.

In addition, blends can be prepared by mixing various amounts of different unpurified or purified activated-polyanionic polysaccharides. These blends are made homogeneous by mixing with overhead stirrers and/or high shear mixers. Unreacted activating agent may be removed from the unpurified mixture by molecular weight sizing, dialysis, dialfiltration or fractional precipitation with a water-soluble solvent, according to standard methods, prior to use. The purified mixture can be used directly for adhesion prevention and/or drug delivery, or may be cast onto flat molds and either air dried or lyophilized to form films or foams.

Film Formation

Polyanionic polysaccharides modified according to the above descriptions can be cast as films in a straightforward manner. Typically the reaction mixture is poured into a vessel having the desired size and shape and allowed to air dry. In general films formed by drying mixtures poured thickly, so that they have a lower surface area/volume, possess greater strength than films formed by drying thinner, higher surface area/volume mixtures.

Alternatively a film can be formed by compressing a gel under conditions that permit escape of water, as, for example, by compressing the gel between two surfaces, at least one of which is porous, as described, for example, in EPO 0 193 510.

If desired, a gel or film can be washed prior to use by, for example, perfusion with water or 1M aqueous sodium chloride. Alternatively the reaction mixture can be dialyzed to remove residual reagents prior to casting as a film. Washing to remove residual reagents or reagent-derived material such as substituted ureas is desirable if the film or gel is to be used for therapeutic applications.

Gels or films colored blue with Brilliant Blue R as described above do not lose their coloration during such washing. The removal of reagents or reaction products can be monitored by high pressure liquid chromatography.

DETAILED DESCRIPTION OF THE INVENTION

The invention is described in more detail in the following examples. These examples are given by way of illustration and are not intended to limit the invention except as set forth in the claims.

EXAMPLE 1

In this example hydrogels were prepared using EDC as an activating agent and leucine methyl ester hydrochloride as a nucleophile.

Sodium hyaluronate (400 mg; 1.0 mmol of carboxyl groups) having a molecular weight between $1 \times 10^6$ and $2 \times 10^6$ was dissolved in 10 ml of distilled water. The pH of the aqueous solution was adjusted to pH 4.75 by addition of 0.1N HCl. Then 314 mg of EDC (1.64 mmol) was added all at once followed by 190 mg (1.05 mmol) of L-leucine methyl ester hydrochloride. The pH of the reaction mixture then rose to 6.2 over two hours. The reaction mixture was kept at room temperature for five hours, after which time it had formed a thick insoluble hydrogel. This hydrogel could be washed with a 1M NaCl solution to remove residual reagents without loss of its physical properties.

EXAMPLE 2

In this example various EDC/leucine:HA ratios were used for comparison of gel formation and properties.

The procedure was as in Example 1, using sodium hyaluronate (400 mg; 1.0 mmol of carboxyl groups) in 15 ml of water. In separate experiments the following quantities of EDC and leucine methyl ester hydrochloride were then added: 153 mg EDC (0.8 mmol)/182 mg leucine methyl ester hydrochloride (1.0 mmol); 76 mg EDC (0.4 mmol)/90 mg leucine methyl ester hydrochloride (0.5 mmol); and 38 mg EDC (0.2 mmol)/45 mg leucine methyl ester hydrochloride (0.25 mmol). Strong hydrogels were obtained as in example 1 for the highest ratio of EDC and leucine methyl ester hydrochloride. At the lowest ratio of reactants (0.2 mmol/0.25 mmol to 1.0 mmol HA carboxyl groups) a weak gel was obtained, which collapsed to a fluid after two weeks.

EXAMPLE 3

In this example the HA concentration was reduced by one-half for comparison of resulting gel properties.

The procedure was as in example 1 except the HA (400 mg; 1.0 mmol of carboxyl groups) was dissolved in 30 ml of water rather than 15 ml (1⅓% w/w HA). A hydrogel was formed, although it was weaker than that obtained in Example 1.

EXAMPLE 4

In this example films were prepared using EDC as an activating agent and leucine methyl ester hydrochloride as a nucleophile.

Sodium hyaluronate (400 mg; 1.0 mmol of carboxyl groups) was dissolved in 40 ml of distilled water. The pH of the solution was adjusted to pH 4.75 by addition of 0.1N HCl. Then EDC (314 mg; 1.64 mmol) was added in a single portion, followed by 190 mg (1.05 mmol) of L-leucine methyl ester hydrochloride. The pH of the reaction mixture rose to 6.2 during two hours, after which time the solution was poured into a petri dish of area 6360 mm$^2$, and allowed to dry to a film over a two day period. Films produced in this manner were strong and insoluble in water and 1M aqueous NaCl. The films could be washed with water or aqueous NaCl as in Example 1 to remove residual reagents without loss of their physical properties. Infrared spectroscopic analysis of such films showed no carbodiimide absorption at about 2130 cm$^{-1}$ and displayed absorptions at about 1740 cm$^1$, 1700 cm$^{-1}$, 1650 cm$^{-1}$, and 1550 cm$^{-1}$.

EXAMPLE 5

In this example various HA concentrations were used in making films for comparison of resulting film properties.

The procedure described in example 4 was repeated, using three different initial HA concentrations made by dissolving the HA (400 mg; 1.0 mmol of carboxyl groups) in 30 ml, 40 ml, or 100 ml of distilled water. Films produced using each of these initial concentrations of HA were strong and insoluble in water and 1M aqueous NaCl, showing that a range of concentrations of HA can be used. Each of these films could be washed with water or aqueous NaCl without loss of its physical properties.

EXAMPLE 6

This example illustrates the effect of dialyzing the reaction mixture prior to casting to form a film, as compared with washing the film after forming it.

Sodium hyaluronate (400 mg in 40 ml of water), EDC (314 mg; 1.64 mmol) and L-leucine methyl ester hydrochloride (190 mg; 1.05 mmol) were allowed to react as in Example 4. Upon completion of reaction (2 hours) the reaction mixture was dialyzed against water, through 12,000 NMW cutoff dialysis tubing in order to remove residual reagents. The dialyzed mixture was then cast as a film as in Example 4. The film so obtained was strong and insoluble in water or 1M aqueous NaCl.

EXAMPLE 7

In this example films were formed by drying more thickly poured reaction mixtures, to compare the properties of films produced from drying mixtures at differing surface area/volume.

A reaction mixture obtained as in Example 4 (40 ml reaction volume) was cast into a small petri dish (area 3330 mm$^2$). The film so obtained was insoluble in 1M aqueous NaCl and in water (100° C.; 1 hour).

EXAMPLE 8

In this example films were prepared using other amino acid esters and HA activated with EDC.

A solution of HA (400 mg in 40 ml of H$_2$O) was brought to pH 4.7 using 0.1N HCl. Then EDC (314 mg; 1.6 mol) was added all at once followed by 1 mmol of the amino acid derivative. The reaction mixture was poured into a petri dish and allowed to dry. Insoluble films were obtained from L-valine methyl ester hydrochloride, L-isoleucine methyl ester hydrochloride, L-proline methyl ester hydrochloride, and L-phenylalanine methyl ester hydrochloride.

EXAMPLE 9

In this example films were prepared using a simple primary amine (aniline) as a nucleophile.

A solution of HA (400 mg in 40 ml of H$_2$O) was brought to pH 4.7 using 0.1N HCl. Then EDC (314 mg; 1.6 mmol) was added all at once followed by 1 mmol of aniline. The reaction mixture was poured into a petri dish and allowed to dry, and insoluble films were obtained.

EXAMPLE 10

In this example films were prepared using other esters of leucine.

A solution of HA (400 mg in 40 ml of H$_2$O) was brought to pH 4.7 using 0.1N HCl. Then EDC (314 mg; 1.6 mmol) was added all at once followed by 1 mmol of the leucine ester. The reaction mixture was poured into a petri dish and allowed to dry. Insoluble films were obtained from both L-leucine ethyl ester hydrochloride and L-leucine t-butyl ester hydrochloride.

EXAMPLE 11

In this example gels were prepared using other amino acid methyl esters.

A solution of HA (400 mg in 15 ml of H$_2$O) was brought to pH 4.7 and EDC (314 mg; 1.6 mmol) was added, followed by the amino acid derivative (1 mmol). The reaction mixture formed a thick gel within from 5 to 24 hours. Water insoluble gels were obtained using L-valine methyl ester hydrochloride, L-isoleucine methyl ester hydrochloride, L-arginine methyl ester hydrochloride, L-proline methyl ester hydrochloride, and L-histidine methyl ester hydrochloride.

EXAMPLE 12

In this example films were prepared using an amino acid amide (leucinamide) as a nucleophile.

A solution of HA (400 mg in 40 ml of H$_2$O) was brought to pH 4.7 using 0.1N HCl. Then EDC (314 mg; 1.6 mmol) was added all at once followed by 1 mmol of L-leucinamide hydrochloride. The reaction mixture was poured into a petri dish and allowed to dry and insoluble films were obtained.

EXAMPLE 13

In this example gels were prepared using leucine ethyl ester hydrochloride.

A solution of HA (400 mg in 15 ml of H$_2$O) was brought to pH 4.7 and EDC (314 mg; 1.6 mmol) was added, followed by leucine ethyl ester hydrochloride (1.0 mmol). The mixture formed a thick, water insoluble gel within from 5 to 24 hours.

EXAMPLE 14

In this example films and gels were prepared using ETC as the HA activating agent.

Sodium hyaluronate (400 mg, 1.0 mmol of carboxyl groups) having a molecular weight in the range between $1 \times 10^6$ and $2 \times 10^6$ daltons was dissolved in water (10 ml and 30 ml). The pH of each aqueous solution was adjusted to pH in 4.75 by addition of 0.1N HCl. Then 475 mg of ETC (1.6 mmol) was added all at once, followed by 190 mg (1.05 mmol) of L-leucine methyl ester hydrochloride. The pH of this reaction mixture rose to pH 6.2 over the next 2 hours. The reaction mixture containing 10 ml of water formed an insoluble gel. The reaction mixture containing 30 ml of water gave an insoluble film after drying.

EXAMPLE 15

This example illustrates the preparation of a colored film.

A solution of HA (400 mg in 30 ml of $H_2O$) was brought to pH 4.75 as in example 13 and then ETC (475 mg; 1.6 mmol) and leucine methyl ester hydrochloride (190 mg; 1.05 mmol) were added. A dilute solution of "Serva Blue" (5 mg/ml) dye in $H_2O$ (0.5 ml) was then added to the reaction mixture. The resulting mixture was poured into a Petri dish and a water insoluble blue film was obtained after 16 hours. The blue color was retained by the film when the film was washed with 1M NaCl and then with $H_2O$.

EXAMPLE 16

This example illustrates the tissue biocompatibility of a film of chemically modified HA.

Four strips of films prepared according to the procedure described in Example 4, and two USP negative control strips were surgically implanted into the paravertebral muscle of White New Zealand rabbits (two per test). The test sites were evaluated either macroscopically after 72 hours or with complete histopathology after 7 days. In accordance with the USP XXI, p. 1237, the test material met the requirements of the USP Implantation Test for the Evaluation of Plastic Materials.

EXAMPLE 17

This example illustrates the preparation of lysine-modified HA.

A 0.4% (w/w) solution of HA in water was prepared. The pH of this solution was adjusted to between 4.3 and 4.75 by addition of acid. To each 100 ml of this solution was added 0.76 g of EDC with stirring until the EDC had completely dissolved. To each 100 ml of the HA/EDC solution was added 0.20 g of lysine methyl ester (LME) with stirring until the LME had completely dissolved. The addition of HA, EDC, and LME was conducted at room temperature; once the final HA/EDC/LME solution had been formed, it was stored at 4° C. until needed.

The LME-modified HA material can be processed into various shapes, sizes, and consistencies depending on the end application. If a thin sheet of the material is desired, the mixture can be poured onto a flat surface. This material can then be turned into a solid by allowing the water to evaporate under ambient or elevated temperatures. An alternative method of producing sheets of the material is to subject it to freeze drying. The pore size of the final product can be controlled by adjusting the initial freezing temperature. Curved surfaces and other shapes can be produced in a similar manner by initially casting the gel onto a negative image surface and then processing as described. The dried sheet can be processed further, if desired, by pressing to a defined thickness in a Carver laboratory press. This is particularly useful for applications requiring placing a thin film between anatomical structures where space is limited.

Mechanical testing of the freeze-dried material, rehydrated in normal saline, resulted in force to break values of 170–900 g/cm$^2$. The elongation to break values for this material were between 33 and 62%.

EXAMPLE 18

This example illustrates the preparation of CMC-modified HA.

HA (0.4% w/w, 0.01M) and Aqualon-type CMC having a molecular weight of 250,000 and a degree of substitution in the range 0.65 to 0.90 (0.19% w/w, 0.01M) were mixed together in aqueous solution at room temperature. The pH of the mixture was adjusted to and maintained at pH 4.7–4.8 by addition of 1M HCl. To each 100 ml of this solution was added 0.67 g (0.04M) EDC. During reaction with EDC, the pH of the solution was maintained at pH 4.7–4.8 by addition of 0.1M HCl and the reaction allowed to proceed for 1 hour, during which time a precipitate formed. The unreacted EDC was removed from the precipitate by dialysis against acidified water (pH 4.0) for 24 hours with 2 dialysate changes at 3 and 19 hours. The HA/CMC slurry was then cast into flat molds and air dried for 24 hours at room temperature.

HA/CMC membranes were shown to reduce the incidence of postoperative adhesion formation in experimental animal models. In experiments using the rat cecal abrasion model, HA/CMC membranes were placed around surgically abraded rat ceca; previous studies had demonstrated that adhesions readily formed to the ceca of rats which had been abraded in controlled fashion. Cecal adhesions in animal groups that received either HA/CMC membranes or ORC membranes (Interceed TC7 membranes marketed by Johnson & Johnson for adhesion prevention) were compared to adhesion controls in animals whose ceca were abraded but did not receive any membrane. The results of these experiments showed that the HA/CMC membranes consistently reduced adhesion formation compared to control animals and to animals that received the Interceed TC7 film.

EXAMPLE 19

This example illustrates the preparation of EDC-activated HA.

HA ($1.0 \times 10^6$ daltons) was dissolved in water to make a 0.8% w/v solution by stirring overnight at 25° C. The pH of the reaction mixture was adjusted to pH 4.75 with 0.1N HCl. EDC (4:1 molar ratio of EDC to HA, 1.53% w/v final concentration) was added to this solution with continuous stirring and was maintained at a constant pH (4.7–5.1) for one hour by adding additional 0.1N HCl. Removal of the unreacted EDC and other low molecular weight impurities was performed by either molecular weight sizing, dialysis, or dialfiltration using standard methods. A water-insoluble, clear gel was obtained after this process.

EXAMPLE 20

This example illustrates the effect of fractional precipitation of EDC-activated HA with a water soluble solvent.

The procedure described in example 19 was repeated with the exception that unreacted EDC and other low molecular weight impurities were removed by fractional precipitation using a suitable water-soluble solvent (e.g., $C_1$–$C_3$ alcohols, acetone). Under these conditions, water insoluble fibers were produced.

EXAMPLE 21

This example illustrates the preparation of EDC-activated CMC.

CMC (250×10³ daltons) was dissolved in water to make a 0.8% w/v solution by stirring at room ambient temperature (22–25° C.) overnight. The pH of the reaction mixture was adjusted to pH 4.75 with 0.1N HCl. EDC (4:1 molar ratio of EDC to CMC, 1.53% W/V final concentration) was added to this solution with constant stirring and the pH was maintained between 4.70 and 5.10 for one hour by adding additional 0.1N HCL. Removal of the unreacted EDC and other low molecular weight impurities was performed by either molecular weight seizing chromatography, dialysis, dialfiltration, or fractional precipitation of the CMC with a suitable water-soluble solvent (e.g., $C_1$–$C_3$ alcohols, acetone). Water insoluble fibers, approximately 300–800 μm long and 10–20 μm wide, are produced from these reaction conditions.

EXAMPLE 22

This example illustrates the preparation of a blend of EDC-activated HA with EDC-activated CMC.

EDC-activated HA and CMC were prepared separately as described in Examples 19 and 21 but each reaction product was not purified prior to blending. Three hundred ml of the activated HA and 300 ml of the activated CMC were placed in a 1000 ml beaker and blended with a Turrax brand blender at 6000 rpm for 10 minutes at 25° C. This resulted mixture was purified by dialysis against pH 4.0 water for 24 hours at a 20:1 ratio with 3 dialysate exchanges. After dialysis the mixture was poured into a flat mold and air dried to a thin water insoluble film. The quantity of fibers in the mixture can be controlled by varying the relative amount of activated CMC and activated HA that are blended together.

Use

Films, foams, or gels of the invention can be used as a surgical aid, to prevent adhesions or accretions of body tissues during a post-operation or healing period, following procedures known in the surgical arts, as described, for example, in DeBelder et al., PCT Publication No. WO 86/00912. During surgery one or more pieces of the gel or film, as appropriate, are inserted or injected between or among the tissues that are to be kept separate.

Films or gels of the invention can also be used for sustained release drug delivery. The drug to be delivered can be covalently bonded to the gel or film, as described, for example, in R. V. Sparer et al., 1983, Chapter 6, pages 107–119, in T. J. Roseman et al., *Controlled Release Delivery Systems,* Marcel Dekker, Inc., New York; and the gel or film can then be implanted or injected at the locus where delivery is desired.

Other Embodiments

Other embodiments are within the following claims.

What is claimed is:

1. A method of preventing tissue adhesions comprising inserting between two tissues to be kept separated a water insoluble biocompatible composition made by combining carboxymethylcellulose and a carbodiimide in an aqueous solution at a pH below 8.0 and a molar ratio of carboxyl groups of carboxymethylcellulose to carbodiimide of one to at least about four.

2. The method of claim 1, wherein the carbodiimide is 1-ethyl-3-(3-dimethylaminopropyl)carbodiimide.

3. The method of claim 1, wherein the carbodiimide is 1-ethyl-3-(3-dimethylaminopropyl)carbodiimide methiodide.

4. The method of claim 1, 2, or 3, wherein the water insoluble biocompatible composition is in the form of a gel.

5. The method of claim 4, wherein a drug is covalently bonded to the gel.

6. The method of claim 4, wherein a drug is admixed into the gel.

7. The method of claim 1, 2, or 3, wherein the water insoluble biocompatible composition is in the form of a film.

8. The method of claim 7, wherein a drug is covalently bonded to the film.

9. The method of claim 7, wherein a drug is admixed into the film.

10. The method of claim 1, 2, or 3, wherein the water insoluble biocompatible composition is in the form of a foam.

11. The method of claim 10, wherein a drug is covalently bonded to the foam.

12. The method of claim 10, wherein a drug is admixed into the foam.

13. A method of preventing tissue adhesions comprising inserting between two tissues to be kept separated a water insoluble biocompatible composition made by combining carboxymethylamylose aid a carbodiimide in an aqueous solution at a pH below 8.0 and a molar ratio of carboxyl groups of carboxymethylamylose to carbodiimide of one to at least about four.

14. The method of claim 13, wherein the carbodiimide is 1-ethyl-3-(3-dimethylaminopropyl)carbodiimide.

15. The method of claim 13, wherein the carbodiimide is 1-ethyl-3-(3-dimethylaminopropyl)carbodiimide methiodide.

16. The method of claim 13, 14, or 15, wherein the water insoluble biocompatible composition is in the form of a gel.

17. The method of claim 16, wherein a drug is covalently bonded to the gel.

18. The method of claim 16, wherein a drug is admixed into the gel.

19. The method of claim 13, 14, or 15, wherein the water insoluble biocompatible composition is in the form of a film.

20. The method of claim 19, wherein a drug is covalently bonded to the film.

21. The method of claim 19, wherein a drug is admixed into the film.

22. The method of claim 13, 14, or 15, wherein the water insoluble biocompatible composition is in the form of a foam.

23. The method of claim 22, wherein a drug is covalently bonded to the foam.

24. The method of claim 22, wherein a drug is admixed into the foam.

* * * * *